US00PP21079P3

(12) United States Plant Patent
Miller

(10) Patent No.: US PP21,079 P3
(45) Date of Patent: Jun. 22, 2010

(54) ***ERODIUM* PLANT NAMED 'CLARET'**

(50) Latin Name: *Erodium chamaedryoides×Geranium cinereum var.*
Varietal Denomination: Claret

(76) Inventor: Luen Miller, 316 Berkeley Way, Santa Cruz, CA (US) 95062

( * ) Notice: Subject to any disclaimer, the term of this patent is extended or adjusted under 35 U.S.C. 154(b) by 18 days.

(21) Appl. No.: 12/148,167

(22) Filed: Apr. 16, 2008

(65) Prior Publication Data

US 2009/0265823 P1 Oct. 22, 2009

(51) Int. Cl.
*A01H 5/00* (2006.01)

(52) U.S. Cl. ..... Plt./263.1

(58) Field of Classification Search ..... Plt./263.1, Plt./324

See application file for complete search history.

*Primary Examiner*—June Hwu

(57) ABSTRACT

A new cultivar of *Erodium* plant named 'CLARET' that is characterized by low compact spreading habit, saturated dark red flowers with prominent deep purple veins and a white eye, and soft gray-green pubescent foliage. In combination these traits set 'CLARET' apart from all other varieties of *Erodium* known to the inventor.

2 Drawing Sheets

Botanical classification: Genus: *Erodium×Geranium.*

Genus and species: *Erodium chamaedryoides×Geranium cinereum* var. *subcaulescens.*

Denomination: 'CLARET'.

BACKGROUND OF THE INVENTION

The present invention relates to a new and distinct cultivar of *Erodium×Geranium* which is grown as an ornamental plant for use in border, rock garden, container, or as a groundcover for the landscape. Although the cultivar was developed by the inventor by the deliberate hybridization between the two genera *Erodium* and *Geranium* as further described herein, the overall appearance of the cultivar is strongly indicative of the genus *Erodium*. Plants of the genus *erodium* are commonly known as alpine *geraniums* or as cranesbill, or storksbill, or heronsbill. The new variety is known botanically as *Erodium chamaedryoides×Geranium cinereum* var. *subcaulescens*,, and will be referred to hereinafter by the cultivar name 'CLARET'.

'CLARET' is the product of a formal breeding program established by the inventor in 2000 at the inventor's nursery in Watsonville, Calif. The purpose of the breeding program was to produce a novel and useful color break in *erodium.* The variety of *erodium* known as 'Bishop's Form' (unpatented) carries attractive pink-red flowers, and the inventor intended to produce a hybrid of 'Bishop's Form' whose flowers would be a deeper and more intense red in color.

'CLARET' is a seedling selection arising from the inventor's controlled cross-pollination of an unnamed seedling of the dark red flowered *Geranium cinereum* var. *subcaulescens* (species, unpatented) as male parent with the pink-red flowered variety *Erodium* 'Bishop's Form' (unpatented) as female parent.

The breeding process which produced 'CLARET' proceeded as follows:

First, in 2000 the inventor transferred pollen from the male parent to the female parent. Pollination was successful and a small amount seed was harvested in 2001. The inventor stored the seed for one year, and it was sown in 2002. The inventor observed the resulting seedlings as they flowered during the summer of 2002. Only one of the seedlings was considered distinct. This seedling exhibited the characteristic habit of the female parent and bore deep red flowers of even greater darkness and saturation than the male parent. The inventor isolated this one seedling and allowed it to grow and multiply by natural basal branching. In 2005, at his nursery in Watsonville, Calif., the inventor carried out the first asexual reproduction of the grown-on seedling, by taking softwood cuttings from the spreading crown. The inventor observed the resulting plants and determined that all the plants exhibited the exact characteristics of the original selected seedling. The inventor named the new plant 'CLARET' and has determined that 'CLARET' is stable, uniform, and reproduces true to type in successive generations of asexual propagation.

'CLARET' is distinguishable from the female parent by the color of the flower. Whereas the flowers of the female parent are mid-pink in color, the flowers of 'CLARET' are deep red in color. The female parent, *Erodium* 'Bishop's Form' is also the closest variety of *erodium* known to the inventor.

'CLARET' is distinguishable from the male parent by habit, flower color, and flower size. Whereas the male parent grows to approximately 20 cm in height and bears dark red flowers whose diameter is approximately 30 mm to 35 mm, plants of 'CLARET' grow only to a height of 6 cm to 8 cm, and the flowers of 'CLARET' are a deeper saturated red in color and are approximately 22 mm in diameter. In addition, the flowers of 'CLARET' exhibit a strongly contrasting white "eye" which is typically absent or very small on flowers of *Geranium cinereum* var. *subcaulescens.*

SUMMARY OF THE INVENTION

The following traits have been repeatedly observed in coastal California and represent the distinguishing characteristics of the variety 'CLARET'. These traits in combination distinguish 'CLARET' from all other varieties of *erodium* known to the inventor. The new invention has not been tested under all possible conditions and phenotypic differences may be observed with variations in environmental, climatic, and cultural conditions, however, without any variance in genotype.

1. 'CLARET' exhibits low compact spreading habit.
2. 'CLARET' exhibits saturated dark red flowers with prominent deep purple veins and a white eye.
3. 'CLARET' exhibits soft gray-green pubescent foliage.
4. 'CLARET' has a long blooming period, profusely from spring to fall, and sporadically in the rest of the year. It is unusual for 'CLARET' to carry no flowers at all.
5. 'CLARET' is 6 cm to 8 cm in height and 20 cm. in diameter at maturity.
6. 'CLARET' is known to be hardy to USDA Zone 7. Further hardiness testing (in colder climates) has not yet been determined.

BRIEF DESCRIPTION OF THE DRAWINGS

The accompanying color drawings illustrate the overall appearance of the new *Erodium* variety named 'CLARET' showing the colors as true as is reasonably possible to obtain in colored reproductions of this type. The plants in the drawings are 18 months old and have been grown in 2 liter containers out-of-doors in Watsonville, Calif.

The drawing labeled

The drawing labeled

Figure 1:
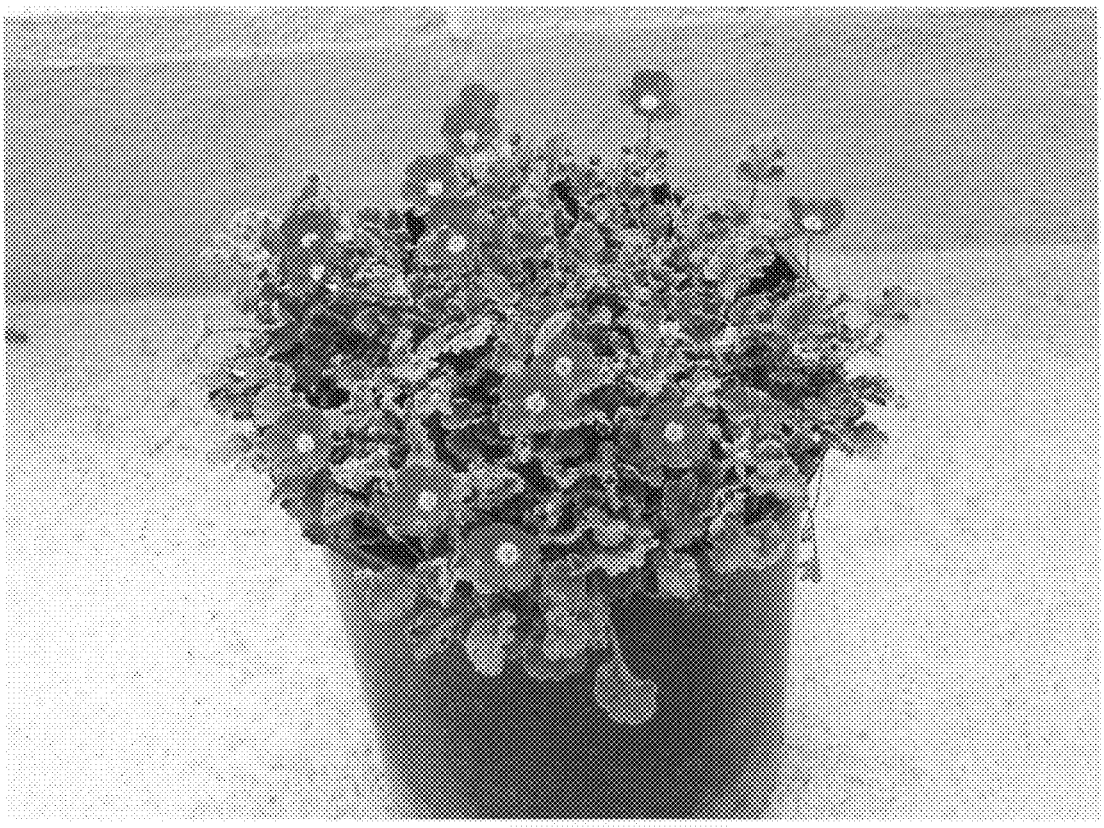
FIG. 1 depicts whole plant of 'CLARET'.
Figure 2:
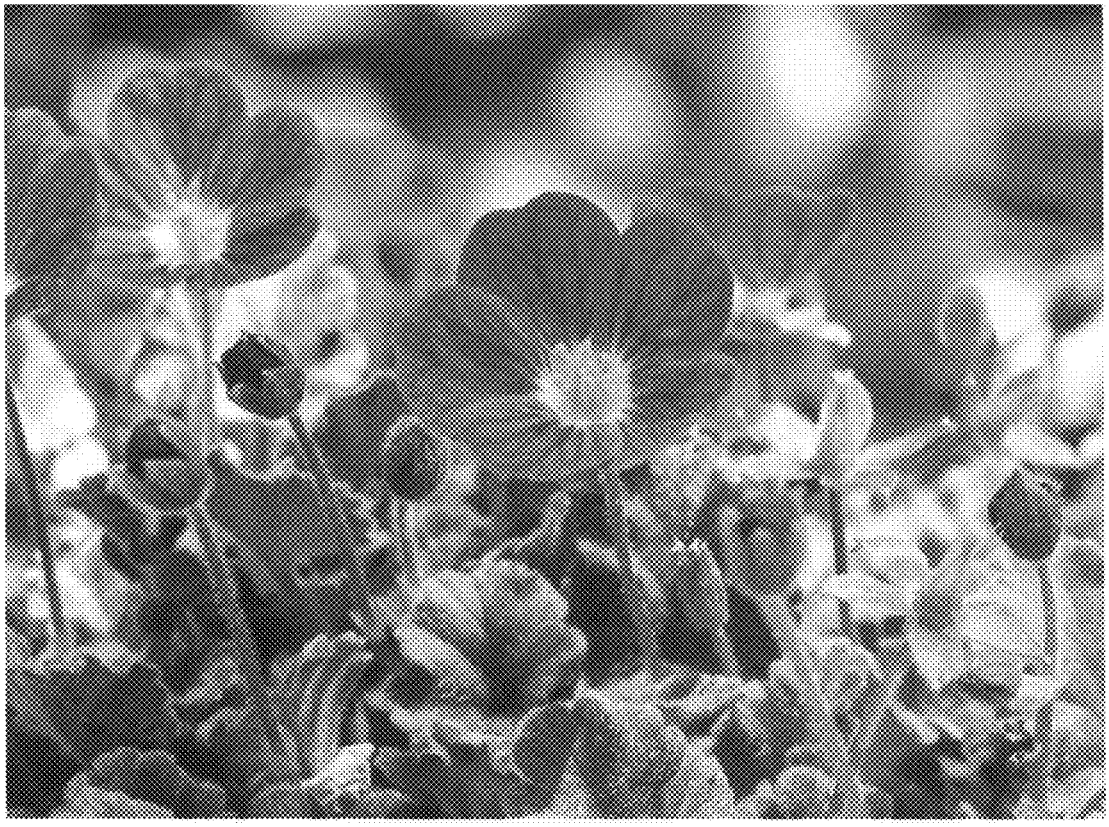
FIG. 2 depicts a close-up view of the flower and foliage of 'CLARET'.

Colors in the photographs may differ from the values cited in the detailed botanical description, which accurately describe the actual colors of the new *Erodium* variety named 'CLARET'. All photographs are taken using conventional photographic techniques and although colors may appear different from actual colors due to light reflectance, they are as accurate as possible by conventional photography.

BOTANICAL DESCRIPTION OF THE PLANT

The following is a detailed description of the new *Erodium* cultivar 'CLARET'. Data was collected in Santa Barbara, Calif. from 18-month-old plants which had been grown out-of-doors in 2-litre containers in Watsonville, Calif. Color determinations are in accordance with the 2001 Royal Horticultural Society Colour Chart of London, England except where general color terms of ordinary dictionary significance are used. The growing requirements are similar to the species.

Botanical classification: *Erodium chamaedryoides*×*Geranium cinereum* var. *subcaulescens*

Denomination: 'CLARET'.

Common names: Alpine *geranium*, Cranesbill, Heronsbill, Storksbill.

Parentage: 'CLARET' is a seedling selection arising from the deliberate cross-pollination of the following parents:

*Female parent.*—*Erodium* 'Bishop's Form'.

*Male parent.*—*Geranium cinereum* var. *subcaulescens.*

Plant type: Perennial.

Plant use: Border, rock garden, container or groundcover for the landscape.

Plant vigor: Moderate.

Root system: Shallow taproot, approximately 8cm long; secondary roots fine and fibrous.

Plant habit: Low, compact and spreading.

Plant dimensions: 6 cm–8 cm. in height and 22 cm. in diameter.

Plant hardiness: Hardy to at least USDA Zone 7.

Seasonal interest: Bright fuchsia-red flowers spring, summer, and fall.

Asexual propagation method: Softwood cuttings and division.

Special needs: Cut back after flowering to induce fresh flush of foliage and flowers.

Cultural requirements: Freely-draining soils, full sun, and adequate but not excess water.

Rooting time: 4–6 weeks in soil and air temperatures between 15° C. and 25° C.

Crop time: A range of 4–6 months is needed to produce a finished 1-litre commercial container plant from a rooted cutting.

Susceptibility or resistance to pests and disease: No known susceptibility or resistance to pests or diseases known to the inventor.

Stem:

*Branching pattern.*—Initially, compact basal rosette, then growing with semi-erect and decumbent many-branched stems.

*Stem shape.*—Cylindrical.

*Stem color.*—146C.

*Stem surface.*—Pubescent.

*Stem length.*—Average of 3 cm.

*Stem diameter.*—Average of 3 mm.

Foliage:

*Leaf arrangement.*—Opposite.

*Leaf division.*—Palmate.

*Leaf shape.*—Reniform.

*Leaf base.*—Auriculate.

*Leaf Apex.*—Rounded apex.

*Leaf margin.*—Palmatifid margin.

*Leaf color* (*adaxial surface*).—N138B.

*Leaf color* (*abaxial surface*)—143A.

*Leaf surface* (*adaxial and abaxial surfaces*).—Pubescent.

*Leaf appearance* (*adaxial and abaxial surfaces*).—Soft velvety appearance.

*Leaf length.*—Ranges from 15 mm to 18 mm.

*Leaf width.*—Ranges from 14 mm to 18 mm.

*Leaf venation.*—Pinnipalmate.

*Vein color* (*adaxial surface*).—N138B

*Vein color* (*abaxial surface*).—143A.

*Leaf attachment.*—Petiolate.

*Petiole length.*—Ranges from 2.0 cm. to 4.0 cm.

*Petiole diameter.*—1 mm.

*Petiole shape.*—Cylindrical.

*Color of petiole.*—Ranges between N144A and N144C.

*Petiole surface.*—Pubescent.

*Stipules.*—None observed.

*Foliar fragrance.*—None observed.

Flower:

*Inflorescence.*—Umbel.

*Flower quantity.*—2 flowers per inflorescence.

*Flower arrangement.*—Cymule.

*Flower shape.*—Rotate.

*Flower dimensions.*—22 mm in diameter and 8 mm. in depth.

*Aspect.*—Facing upward and outward.

*Self-cleaning or persistent.*—Readily self-cleaning.

*Lastingness of the flowers.*—Approximately 5 days.

*Flower color.*—Both 61A and 61B are individually present. Flower has eye, 145D, diameter approximately 4mm.

*Petals.*—Five in number.

*Petal dimensions.*—10 mm. in length and 9 mm. in width.
*Petals fused or unfused.*—Unfused.
*Petal margin.*—Entire.
*Petal apex.*—Emarginate.
*Petal base.*—Cuneate.
*Petal shape.*—Obcordate.
*Petal surface* (*abaxial and adaxial surfaces*).—Glabrous.
*Petal color* (*both surfaces*).—61A and 61B both present. 2 mm basal portion 145D and forms "eye" of flower.
*Petal veins.*—Pronounced radial and branching, color (both surfaces) N79B.
*Peduncle shape.*—Cylindrical.
*Peduncle surface.*—Pubescent.
*Peduncle length.*—Ranges from 4.0 cm. to 4.5 cm.
*Peduncle diameter.*—0.75 mm.
*Peduncle color.*—173A.
*Pedicel shape.*—Cylindrical.
*Pedicel surface.*—Lanate.
*Pedicel colour.*—173A.
*Pedicel dimensions.*—15 mm–18 mm in length and 0.75 mm in diameter.
*Stipules* (*at junction of pedicel and peduncle*).—3 in number.
*Stipule dimensions.*—1.5 mm–2.0 mm in length and 1.5 mm. in width.
*Stipule surface.*—Pubescent.
*Stipule shape.*—Ensiform.
*Stipule apex.*—Acuminate.
*Stipule base.*—Truncate.
*Stipule colour.*—146D.
*Bud color.*—143A.
*Bud shape.*—Ovoid.
*Bud surface.*—Villous.
*Bud dimensions.*—5 mm. in length and 2.5 mm. in width.
*Bud apex.*—Rounded.
*Calyx shape.*—Stellular.
*Calyx diameter.*—13 mm.
*Sepals.*—5 in number, persistent.
*Sepal dimensions.*—7 mm. in length and 2 mm. in width.
*Sepal margin.*—Entire.
*Sepal surface.*—Villous.
*Sepal shape.*—Ovate.
*Sepals fused or unfused.*—Unfused.
*Sepal apex.*—Aristate.
*Sepal base.*—Truncate.
*Sepal color* (*adaxial and abaxial surfaces*).—143A.
*Flower fragrance.*—None observed.

Reproductive organs:

*Stamens.*—Ten stamens (5 fertile stamens alternating with 5 shorter sterile staminodes, all united at base.
*Stamen color.*—155A.
*Stamen dimensions.*—Fertile stamens 5 mm in length and approximately 0.5 mm in diameter; staminodes 2.5 mm in length and slightly thicker than fertile stamens.
*Pistil.*—One in number.
*Pistil shape.*—Urn-shaped.
*Pistil color.*—155A.
*Pistil height.*—3 mm. in height.
*Pollen quantity.*—Minimal.
*Pollen color.*—15C.
*Anther color.*—15C.
*Stigma shape.*—5-pronged.
*Stigma color.*—1A.
*Stigma dimensions.*—1.5 mm. in diameter.
*Ovary position.*—Superior.
*Ovary color.*—150B.
*Ovary shape.*—Ovoid in shape.
*Ovary dimensions.*—2.0 mm. in height and 1.5 mm. in width.
*Seed.*—No seed has been observed to date.

It is claimed:

1. A new and distinct variety of *Erodium* plant named 'CLARET' as described and illustrated herein.

* * * * *